US008323707B2

(12) United States Patent
Friedel et al.

(10) Patent No.: US 8,323,707 B2
(45) Date of Patent: Dec. 4, 2012

(54) TRIGONELLINE AS A MUSCLE STIMULANT

(75) Inventors: Angelika Friedel, Binzen (DE); Karin Kuratli, Reinach (CH); Christof Wehrli, Witterswil (CH); Karin Wertz, Rheinfelden (DE); Swen Wolfram, Waldshut-Tiengen (DE); Ying Wang-Schmidt, Shanghai (CN)

(73) Assignee: DSM IP Assets B.V., Heerlen (NL)

( * ) Notice: Subject to any disclaimer, the term of this patent is extended or adjusted under 35 U.S.C. 154(b) by 130 days.

(21) Appl. No.: 12/959,621

(22) Filed: Dec. 3, 2010

(65) Prior Publication Data

US 2011/0142974 A1 Jun. 16, 2011

Related U.S. Application Data

(63) Continuation-in-part of application No. PCT/EP2010/058124, filed on Jun. 10, 2010.

(30) Foreign Application Priority Data

Jun. 11, 2009 (EP) ........................................ 0916247
Jul. 23, 2009 (EP) ..................................... 09166271

(51) Int. Cl.
*A01N 65/00* (2009.01)
(52) U.S. Cl. ....................................................... 424/725
(58) Field of Classification Search ........................ None
See application file for complete search history.

(56) References Cited

U.S. PATENT DOCUMENTS

| 2003/0003091 A1 | 1/2003 | Gaetani |
| 2005/0176827 A1 | 8/2005 | Lee et al. |
| 2005/0226948 A1 | 10/2005 | Lee et al. |
| 2005/0233014 A1 | 10/2005 | Lee et al. |
| 2006/0002983 A1 | 1/2006 | Matsumoto et al. |
| 2006/0189566 A1 | 8/2006 | Komatsu et al. |
| 2007/0160698 A1 | 7/2007 | Waga et al. |
| 2008/0194553 A1 | 8/2008 | Gillessen |
| 2008/0199517 A1 | 8/2008 | Sunil et al. |

FOREIGN PATENT DOCUMENTS

| DE | 20 2006 019504 U1 | 3/2007 |
| EP | 1 604 671 A1 | 12/2005 |
| WO | WO 01/74361 A1 | 10/2001 |
| WO | WO 2004/037018 A1 | 5/2004 |
| WO | WO 2005/021596 A2 | 3/2005 |
| WO | WO 2005/039546 A2 | 5/2005 |
| WO | WO 2006/096996 A1 | 9/2006 |
| WO | WO 2009/073942 A1 | 6/2009 |

OTHER PUBLICATIONS

Trigonelline, 1 page, 2011.*
"Aide-Prise-Poid. Grossir.—Forum Nutrition", Internet Citation, Apr. 30, 2009, pp. 1-3, XP002546149; retrieved from the internet: URL:http://www. Forum.doctissimo.fr/nutrition/grossir/aid-prise-poid-sujet__14 7967__1.htm [retrieved on Sep. 16, 2009] items 4 and 6;; item 7, par. 3.
"Phtotherapie" Internet citation Jan. 25, 2008, pp. 1-6, XP002546150 retrieved from the internet:URL:http://www.musculationmultisports.com/Plantes%20baseball%20baseball.html [retrieved on Sep. 16, 2009] chapter "Fenugrec" and retrieved from the internet: URL:http://web.archive.org/web/*///http://www.musculationmultisports.com/Plantes%20baseball%20baseball.html [retrieved on Sep. 17, 2009].
International Search Report in PCT/EP2010/058124 mailed Aug. 18, 2010.
International Preliminary Report on Patentability in PCT/EP2010/058124 issued Dec. 12, 2011.

* cited by examiner

*Primary Examiner* — Michael Meller
(74) *Attorney, Agent, or Firm* — Nixon & Vanderhye P.C.

(57) ABSTRACT

This invention relates to the use of trigonelline compounds to increase muscle weight during periods of activity or to inhibit muscle loss during periods of inactivity.

1 Claim, 4 Drawing Sheets

* significant: p ≤ 0.05

TRIGONELLINE AS A MUSCLE STIMULANT

This application is a continuation-in-part of PCT patent application PCT/EP2010/058124, filed Jun. 10, 2010, and claims priority to European Patent Applications EP09162470, filed Jun. 11, 2009, and European Patent Application EP09166271.8 filed Jul. 23, 2009, each of which is hereby incorporated by reference.

FIELD OF THE INVENTION

This invention relates to the use of trigonelline compounds to increase muscle weight during periods of activity or to inhibit muscle loss during periods of inactivity.

BACKGROUND OF THE INVENTION

One of the most characteristic features of skeletal muscle is its remarkable ability to adapt to different stimuli. Throughout life the skeletal muscle is permanently adapting to internal (ageing/sarcopenia resulting in muscle loss) or external changes (physical activity results in muscle hypertrophy; while injury results in muscle recovery; and bed rest results in muscle atrophy). These influences modify structural, biochemical and molecular variables of the different skeletal muscle fibers. For the adaptation of myofibers the activation and myogenic differentiation of satellite cells, the so-called stem cells of the skeletal muscle, are required. After exercise training, for example, satellite cells fuse together with the enlarging or repairing myofibers.

Trigonelline is an alkaloid with chemical formula $C_7H_7NO_2$. Trigonelline is a niacin (vitamin B3) metabolite which is excreted in the urine. Trigonelline is also found in coffee, where it may help to prevent dental caries by preventing the bacteria *Streptococcus mutans* from adhering to teeth.

US 2005/0226948 (Lee et al) discloses a Fenugreek seed extract containing 4-hydroxyisoleucine and a number of other compounds, including trigonelline. These combinations are used to enhance glucose transport into muscle cells.

US2007/0105793 (Hendrix) discloses a composition useful for treatment of hyperlipidemia, hypercholesterolemia and hyperglyceridemia that contains niacin and derivatives.

US2007/0259861 (Krantz) discloses compositions containing a non-steroidal anti-inflammatory drug (NSAID) in combination with a prostaglandin mimetic (which can include various niacin derivatives. These combinations are used for pain and/or inflammation relief.

DESCRIPTION OF THE INVENTION

It has been found, in accordance with this invention that trigonelline can increase muscle weight during a training period, and can reduce muscle loss during periods of lesser activity or immobility. Thus, one aspect of this invention is the use of trigonelline, and/or a salt or ester thereof, in the manufacture of a nutraceutical or food to increase muscle weight during training, or to reduce the amount of muscle loss during inactivity, with the proviso that if the trigonelline is present in a plant extract, then the extract is free from tropane alkaloids. Another aspect of this invention is a method of increasing muscle mass during exercise comprising administering an effective amount of trigonelline or salt or ester thereof to an individual undergoing training and observing a muscle mass increase, proviso that if the trigonelline is present in a plant extract, then the extract is free from tropane alkaloids. A further aspect of this invention is a method of reducing the muscle loss of a less active or immobile person at risk of muscle loss by administering trigonelline or a salt or ester thereof, and observing retention of muscle. In preferred embodiments, the trigonelline and/or salt or ester thereof is used along with an optimal nutritional supply of protein and vitamins (including especially Vitamin D and/or its metabolites such as 25-hydroxyvitamin D3).

Figure 1:
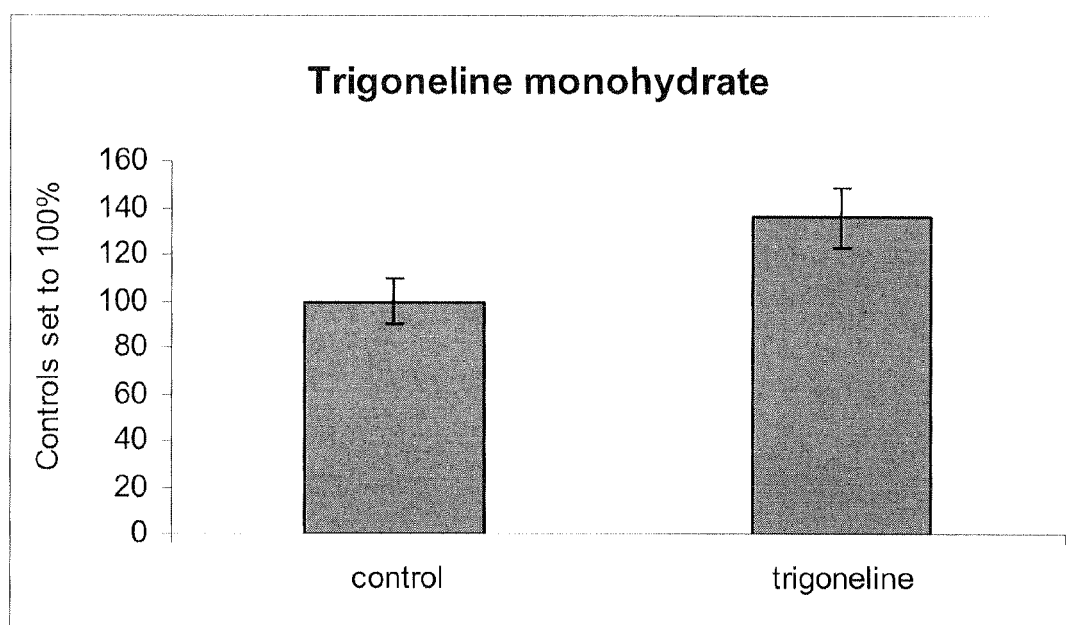
FIG. 1 shows the results of in vitro effects of trigonelline on myotube formation in mouse muscle cells.

As used throughout the specification and claims, the following definitions apply:

"Trigonelline" refers to any form of trigonelline suitable for a nutraceutical, including trigonelline, and trigonelline hydrate of a trigonelline salt or ester.

"Trigonelline salt or ester" refers to any salt or ester form of trigonelline which can be used to formulate trigonelline into a nutraceutically acceptable form, or into a foodstuff. The salt or ester should be one which is allowable for ingestion by the applicable regulatory agency. Examples of suitable trigonelline salts include sulfate, hydrogen sulfate, chloride, phosphate, and citrate. Examples of suitable trigonelline esters include the methyl ester chloride, and ethyl ester chloride.

"Prevent" includes reduction of severity of symptoms and or conditions, reducing the risk of developing a symptom or condition, increasing the time before symptoms or conditions develop, early intervention, as well as negation of a symptom or condition.

"Observing" can be done either by the individual who uses the trigonelline or by a third party. The observation may be done over a period of time, such as for one week, one month, three months, six months or other desired time period.

Trigonelline can be found in a large variety of plants such as green and roasted coffee beans, *Trigonella foenum graecum* (fenugreek, Leguminosae), *Schumanniophyton magnificum*, (Rubiaceae) *Mappia foetida*, and *Strophanthus* spp., to name just a few. Thus, trigonelline may be present in a plant extract. Preferably, if using a plant extract as the source of trigonelline, the plant extract contains at least about 20 wt % of trigonelline and the extract is free from tropane alkaloids.

Alternatively, trigonelline can be made synthetically from nicotinic acid. An example of a synthesis is DE 344030 (1921) "Betaines of the pyridine series" (Merck, E.).

It was found that trigonelline can boost the weight of muscles when used in combination with exercise, and that it can delay the onset of muscle atrophy when muscle is not being used or not being used strenuously.

It is also preferred that if a plant extract is used as the source of trigonelline, then the plant extract is a coffee bean extract, and the amount of trigonelline is at least 10% of the extract by weight.

It is preferred that the trigonelline is used as part of a nutritionally complete diet, i.e. used in conjunction with an adequate or optimal supply of protein and/or vitamins. Preferably the vitamins will include Vitamin D and/or an active Vitamin D metabolite such as 25-hydroxyvitamin D3. Combinations of trigonelline and/or a salt or ester thereof along with protein and/or vitamin(s) are also a part of this invention.

As trigonelline has applications in veterinary medicine as well as human medicine, another aspect of this invention is the use of trigonelline to improve muscle health in non-human animals, particularly racing horses, dogs, camels or other animals used for racing or as pack animals, or other animals used for their strength. The trigonelline can be administered to healthy animals, or to injured/sick animals to speed their convalescence.

Trigonelline or a salt or ester thereof, without introducing calories to the diet, has these specific benefits:
  Helps to prevent muscle loss
  Supports healthy muscle function together with exercise
  Helps to prevent sarcopenia (risk reduction, reduce severity, delay progression)
  Helps to prevent muscle loss during illness or after surgery, thus contributing to faster convalescence and shorter hospital stays
  Helps to prevent frailty in elderly, thus contributing to improved mobility, quality of life and helps to postpone loss of independent living
  Helps one retain muscle development when circumstances prevent one from exercising
  Supports an efficient exercise program
  Supports the efficacy of resistance exercise programs such as bodybuilding or weight training
  Supports recovery from muscle damage
  Helps one retain exercise success/training effects longer
  Helps one maintain one's shape/condition longer
  Helps you to find the physical power you need
  Helps to maintain muscle strength
  Helps to increase muscle strength
  Improves body composition together with exercise
  Supports body toning and body shaping
  Promotes myoblast differentiation
  Promotes muscle differentiation
  Promotes muscle growth
  Promotes muscle formation
  Promotes muscle recovery and repair
  Promotes muscle hypertrophy, when combined with exercise We surprisingly found that trigonelline helps when the skeletal muscle is adapting to stimuli like training—muscle load (hypertrophy) or to unloading (atrophy). It helps to strengthen the effects of training and prevents skeletal muscle loss. Therefore trigonelline supports an efficient training program and promotes muscle hypertrophy when combined with exercise/muscle loading. These effects can be observed.

Thus trigonelline helps to prevent sarcopenia, frailty in elderly, and muscle loss during bed rest due to illness, surgery and longer hospital stays. Furthermore, trigonelline promotes muscle recovery and repair.

Dosages:

While dosages may vary, they may range from at least 5 mg per day for a human; preferably from 5 to 5,000 mg/day for a human, more preferably from 10 to 3000 mg/day for a human and even more preferably from 50-500 mg/day for a human. Other preferred dosages include:
  50-100 mg/day
  75-125 mg/day
  100-150 mg/day
  125-175 mg/day
  200-225 mg/day and
  250-300 mg/day.
  Animal dosages are similar, and can be adjusted accordingly for the weight of the animal.

In accordance with this invention, the trigonelline or salt or ester thereof is present in a dietary, nutraceutical, or pharmaceutical composition. Preferred compositions comprise trigonelline or a salt or ester thereof and a suitable dietary, nutraceutical or pharmaceutical carrier. The dietary products or nutraceuticals of this invention can be in any format acceptable to the consumer, including functional food and beverages.

Examples of suitable nutritional formats include various foods and beverages, including shots, cereal or other bars, drinks, protein-rich drinks, supplements, instant beverages, effervescents and the like. Especially preferred are formats which are suitable for sports nutrition, including beverages, protein powders, bars, supplements and instant beverages.

The following non-limiting Examples are presented to better illustrate the invention.

EXAMPLE 1

Muscle Cell Model

We first tested the influence of trigonelline on myoblast differentiation in vitro using C2C12 mouse myoblast cells which are commonly used to study muscle adaptation. C2C12 cells were seeded on 96 well collagen-I plates (1600 cells/well) in growth medium (Dulbecco's modified Eagle's medium (DMEM) supplemented with 10% FBS, 2 mM L-Glutamine, 1 mM pyruvate, 50 IU/ml penicillin, 50 ug/ml streptavidin) until it reaches 100% confluency, approximately 3 days. Cells were then induced to differentiate using differentiation medium (DMEM, 2% FBS, 2 mM L-Glutamine, 1 mM pyruvate, 50 IU/ml penicillin, 50 ug/ml streptavidin) with either DMSO (control) or 10 µg/ml trigonelline monohydrate for 24 h. Final DMSO concentration was standardized to 0.5% in all wells. Cells were cultured at 37° C., with 5% $CO_2$.

Cells were fixed with 3.7% formaldehyde solution (37% formaldehyde diluted in growth medium, sterile filtered before used) for 10 min. at room temperature, and washed twice with 1×DPBS (1× Dulbecco's Phosphate Buffered Saline). After permeabilization with 0.1% TritonX-100 (diluted in 1×DPBS) for 2 min. the samples were blocked with 1×DPBS plus 2% BSA for 1 h. For myocyte labelling, the cells were labelled with 1:20 anti-alpha-myosin heavy chain antibody (MF-20) for 1 hour. The samples were washed with 1×DPBS and fluorescently labelled with secondary antibody (1:250 Alexa 488 IgG antimouse secondary antibody plus 1:2000 Hoechst in 1×DPBS) for 1 h. Finally, the cells were washed twice with 1×DPBS and plates were sealed for imaging on the ArrayScan® HCS Reader.

For image analysis myosin labelled myotubes were quantified on the ArrayScan HCS Reader using BioApplication Morphology Explorer.V2. Myocytes were selected with Object Area larger than 500 and Object Total Intensity greater than 1000. The number of myocytes from triplicate samples are shown in FIG. 1. Trigonelline was seen to increase the differentiation in C2C12 mouse myoblast cells by 36%.

EXAMPLE 2

In Vivo Effects

To confirm our in vitro results, trigonelline was first tested in a hypertrophy animal model to see the effects during muscle load. The gastrocnemius muscle from one hindlimb of the animals was removed to induce compensatory hypertrophy in the plantaris and soleus muscles by multiple mechanisms. This model increases the muscle weight under muscle load/training. It simulates the human condition of an average human who is physically active or an athlete to support skeletal muscle function during exercise.

Female C57Bl/6 mice were delivered at a weight of 18-20 g and acclimatized to the facilities for a period of one week. At the beginning of the study the animals were randomized into two groups (10 animals per group).

The animals were anesthetized and the left hindlimb of the animals was fixed. A small incision was made through the skin over the gastrocnemius muscle. The complete gastrocnemius muscle and its tendons were exposed. Both heads of the gastrocnemius muscle were carefully dissected from the underlying intact muscles and care was taken not to rupture nerves and vessels. The skin was closed with a silk and the animals were returned separately into their cages. After recovering from anesthesia, the animals could move immediately without problems. All animals received an analgesic. Animals were treated for three weeks by gavage with trigonelline-hydrochloride at a daily dosage of 300 mg/kg BW and the control group received vehicle.

Using this technique we have identified and quantified increased skeletal muscle weight of the plantaris and soleus muscle in the operated (pQCT-measurement) and in the gastrocnemius, plantaris and soleus muscle of the non-operated leg (weight measurement). The hypertrophy in the operated leg is a compensatory reaction of the remaining muscles after the gastrocnemius muscle has been removed. The hypertrophy on the non-operated leg is due to a special training effect, because this leg was used more.

Figure 2:
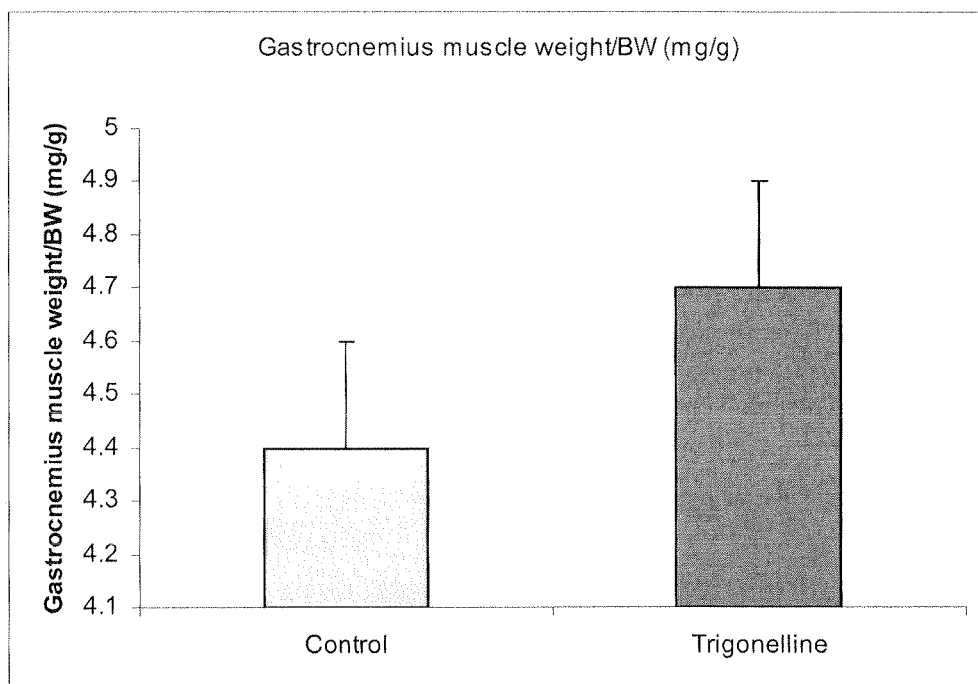
FIG. 2 shows wet weight of the gastrocnemius muscle relative to body weight (BW) from control and treated mice (hypertrophy model).

The wet weight of the non-operated gastrocnemius muscle (relative to the body weight) increased by 7% in the group receiving trigonelline (FIG. 2).

The absolute and the relative (compared to body weight of the animals) wet weight of all analyzed muscles from the non-operated leg were increased.

In the operated leg, the total leg weight and the muscle cross-sectional area, as assessed using computer-tomography measurement were also increased. Data are shown in Table 1.

TABLE 1

| Parameters | Control (n = 10) | Trigonelline-hydrochloride 300 mg/kg/BW (n = 10) |
| --- | --- | --- |
| M. gastrocnemius wet weight (mg) (non-operated leg) | 98.5 | 99.3 |
| M. plantaris wet weight (mg) (non-operated leg) | 12.4 | 13 |
| M. soleus wet weight (mg) (non-operated leg) | 7.1 | 7.2 |
| M. gastrocnemius wet weight/body weight (mg/g) (non-operated leg) | 4.44 | 4.57 |
| M. plantaris wet weight/body weight (mg/g) (non-operated leg) | 0.56 | 0.60 |
| M. soleus wet weight/body weight (mg/g) (non-operated leg) | 0.32 | 0.33 |
| Gastrocnemius-Plantaris-Soleus muscle weight (whole leg)/body weight (mg/g) (non-operatedleg) | 5.32 | 5.50 |
| Total leg cross-sectional area (mm$^2$)- non operated leg | 33.90 | 35.05 |
| Muscle cross-sectional area (mm$^2$)- non operated leg | 26.27 | 32.15 |
| Total leg cross-sectional area (mm$^2$)- operated leg | 25.40 | 26.79 |
| Muscle cross-sectional area (mm$^2$)- operated leg | 19.13 | 23.72 |

These results show that under loading (after surgery of the gastrocnemius the muscle-hypertrophy)/training conditions, skeletal muscle wet weight increased in the animals.

EXAMPLE 3

Muscle Atrophy

To extend our in vitro and in vivo results we were also interested in testing the effects of trigonelline during skeletal muscle unloading (atrophy conditions). Therefore we conducted a second in vivo study were the hindlimbs of the animals were unloaded to induce skeletal muscle atrophy.

Tail suspension leads to skeletal muscle atrophy in the unloaded hindlimbs of the animals. The results can be transferred to the human situation: sarcopenia (degenerative loss of skeletal muscle mass and strength during the process of ageing) or immobilization of skeletal muscle (e.g. after prolonged bed rest).

Female C57Bl/6 mice were delivered at a weight of 18-20 g and acclimatized to the facilities for a period of one week. At the beginning of the study the animals were randomized into two groups (10 animals per group).

Thereafter the groups were placed in special cages and the hindlimbs were unloaded (tail suspension) for a duration of three weeks. All mice were housed separately and had access to feed and water ad libidum. Animals were treated for three weeks by gavage with trigonelline-hydrochloride at a daily dosage of 300 mg/kg/BW and the control group received vehicle.

Figure 3:
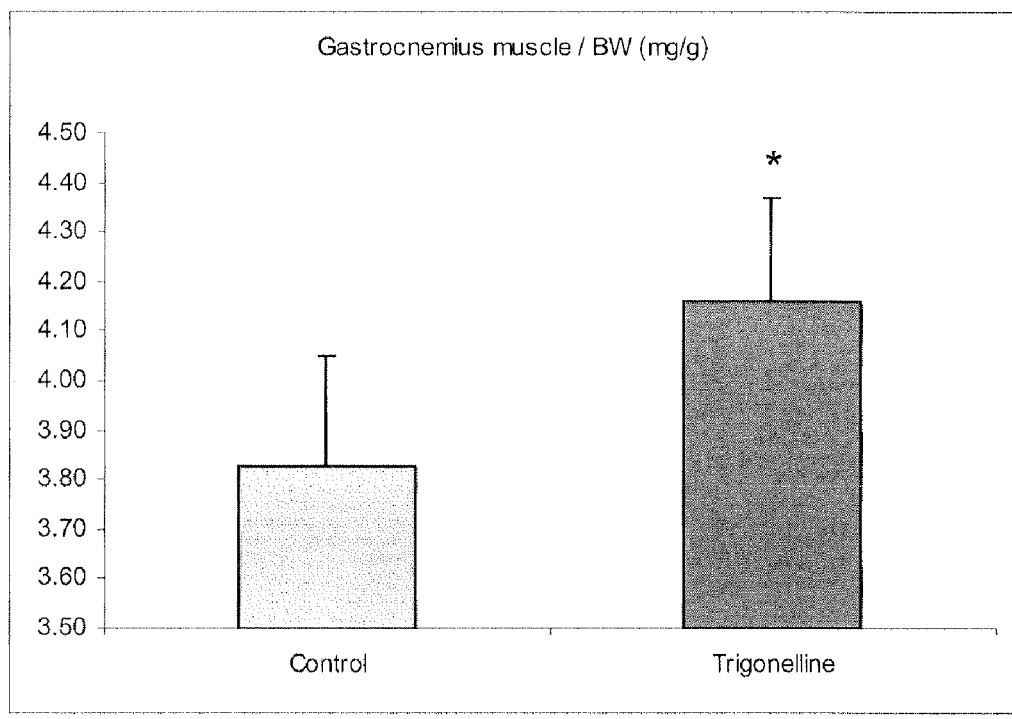
FIG. 3 shows results of the tail suspension model gastrocnemius muscle wet weight relative to BW for control and treated mice.

We found that the wet weight of the gastrocnemius muscle (relative to the body weight) increased by 9% (FIG. 3), a statistically significant result.

We also compared the other two muscles from the operated hindlimb (plantaris muscle and soleus muscle). The results, presented in TABLE 2 below, show an increase of the wet weights of the muscles in animals treated with trigonelline-hydrochloride compared to the control animals (absolute muscle weight). Furthermore, when muscle weights were normalized to the body weights, animals treated with trigonelline-hydrochloride demonstrated an increased muscle weight/body weight ratio (relative muscle weight), i.e, an improved body composition. The total weight for muscles in one leg was also significantly increased when treated with trigonelline-hydrochloride (whole leg relative to body weight). Computer tomography measurements of total and muscle leg area confirmed that trigonelline-hydrochloride treatment increases skeletal muscle mass.

TABLE 2

| Parameters | Control (n = 10) | Trigonelline-hydrochloride 300 mg/kg/BW (n = 10) |
| --- | --- | --- |
| M. gastrocnemius wet weight (mg) | 78.13 | 86.01 * |
| M. plantaris wet weight (mg) | 9.84 | 10.53 |
| M. soleus wet weight (mg) | 4.29 | 4.62 |
| M. gastrocnemius wet weight/body weight (mg/g) | 3.83 | 4.16 * |
| M. plantaris wet weight/body weight (mg/g) | 0.48 | 0.51 * |
| M. soleus wet weight/body weight (mg/g) | 0.21 | 0.22 |
| Gastrocnemius-Plantaris-Soleus muscle weight (whole leg)/body weight (mg/g) | 4.52 | 4.89 * |
| Total leg cross-sectional area (mm$^2$) | 29.1 | 30.4 |
| Muscle cross-sectional area (mm$^2$) | 26.6 | 27.8 |

* significant: $p \leq 0.05$

The results show that under unloading/atrophy of the animal total leg cross-sectional area, the muscle weights increase; i.e. more of the muscle mass is retained during inactivity in trigonelline-supplemented animals versus controls.

EXAMPLE 4

Endurance

To test the effect of trigonelline in non-trained animals, we performed a maximal endurance test after a treatment period of three weeks.

Female C57Bl/6 mice were delivered at a weight of 18-20 g and acclimatized to the facilities for a period of one week. At the beginning of the study the animals were randomized into two groups (10 animals per group). All mice were housed separately and had access to feed and water ad libidum. Animals were treated for three weeks by gavage with trigonelline-hydrochloride at a daily dosage of 300 mg/kg/BW and the control group received vehicle.

For acclimatization, animals were placed on the treadmill for 5 minutes after two weeks. The maximal endurance test was performed two day before the section of the animals.

Figure 4:
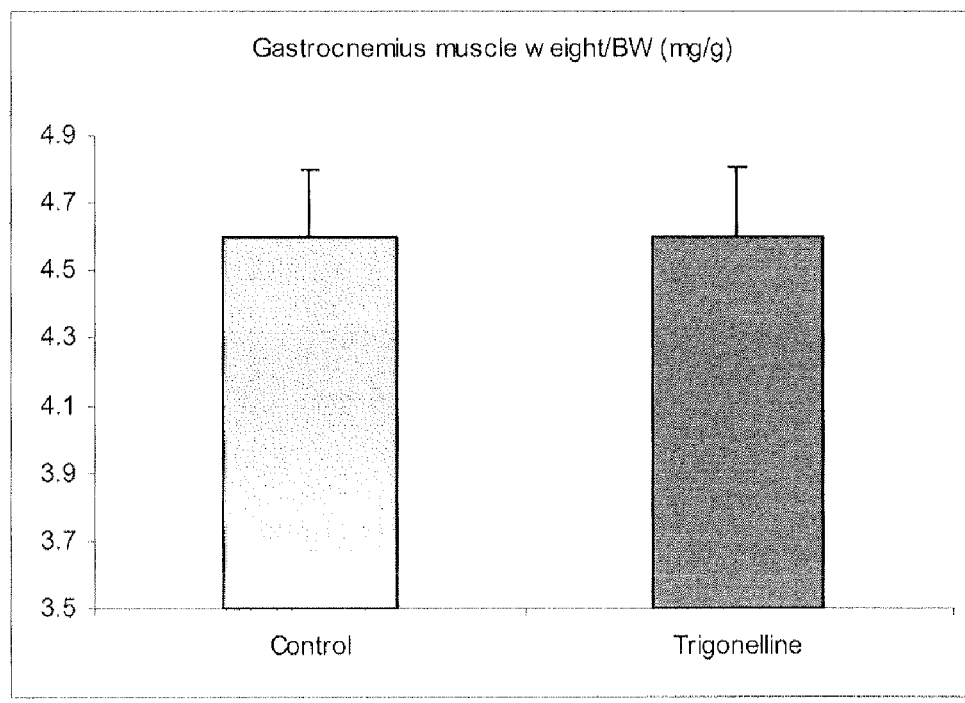
FIG. 4 shows wet weight of gastrocnemius muscle after treadmill running.

We found that the wet weight of the gastrocnemius muscle was equal in both groups (FIG. 4), as was the wet weight of the other muscles assessed (data not shown). Also, endurance of untrained animals was not influenced by 3 weeks of trigonelline supplementation.

| Parameters | Control (n = 10) | Trigonelline-hydrochloride 300 mg/kg/BW (n = 10) |
| --- | --- | --- |
| Mean running time (minutes) | 39.00 | 38.70 |
| M. gastrocnemius wet weight (mg) | 100.65 | 100.66 |
| M. plantaris wet weight (mg) | 12.16 | 12.12 |
| M. soleus wet weight (mg) | 6.28 | 6.29 |
| M. gastrocnemius wet weight/body weight (mg/g) | 4.64 | 4.57 |
| M. plantaris wet weight/body weight (mg/g) | 0.56 | 0.55 |
| M. soleus wet weight/body weight (mg/g) | 0.29 | 0.29 |
| Gastrocnemius-Plantaris-Soleus muscle weight (whole leg)/body weight (mg/g) | 5.49 | 5.41 |

These results show that trigonelline has no effect on endurance and skeletal muscle mass in untrained mice.

What is claimed is:

1. A method of increasing muscle mass in combination with an exercise selected from the group consisting of resistance training, bodybuilding or weight training in a human in need thereof consisting essentially of administering therapeutically effective amounts of a coffee bean extract which consists of at least 20 wt. % of trigonelline and 25-hydroxyvitamin D3 with the proviso that the extract is free from tropane alkaloids to said human.

* * * * *